US00PP23473P2

(12) United States Plant Patent
Blom

(10) Patent No.: US PP23,473 P2
(45) Date of Patent: Mar. 12, 2013

(54) ***ECHINACEA* PLANT NAMED 'GUAVA ICE'**

(50) Latin Name: *Echinacea hybrida*
Varietal Denomination: Guava Ice

(76) Inventor: Arie Blom, Oudewater (NL)

( * ) Notice: Subject to any disclaimer, the term of this patent is extended or adjusted under 35 U.S.C. 154(b) by 106 days.

(21) Appl. No.: 13/068,695

(22) Filed: May 17, 2011

(51) Int. Cl.
*A01H 5/00* (2006.01)

(52) U.S. Cl. ..... Plt./428
(58) Field of Classification Search ..... Plt./428
See application file for complete search history.

*Primary Examiner* — June Hwu
(74) *Attorney, Agent, or Firm* — C. A. Whealy

(57) ABSTRACT

A new and distinct cultivar of *Echinacea* plant named 'Guava Ice', characterized by its upright plant habit; moderately vigorous growth habit; freely basal branching habit; strong flowering stems; early and freely flowering habit; large anemone-type inflorescences with greyed red to red-colored ray and orange red-colored disc florets; and good garden performance.

3 Drawing Sheets

Botanical designation: *Echinacea hybrida.*
Cultivar denomination: 'GUAVA ICE'.

BACKGROUND OF THE INVENTION

The present invention relates to a new and distinct cultivar of *Echinacea* plant, botanically known as *Echinacea hybrida*, and hereinafter referred to by the name 'Guava Ice'.

The new *Echinacea* plant is a product of a planned breeding program conducted by the Inventor in Vleuten and Zuidwolde, The Netherlands. The objective of the breeding program is to develop new freely branching and freely flowering *Echinacea* plants with large centers and attractive ray and disc floret coloration.

The new *Echinacea* plant originated from an open-pollination in July, 2006 in Vleuten, The Netherlands of a proprietary selection of *Echinacea hybrida* identified as code number Ec 512-004, not patented, as the female, or seed, parent with an unknown selection of *Echinacea hybrida* as the male, or pollen, parent. The new *Echinacea* plant was discovered and selected by the Inventor as a single flowering plant from within the progeny of the stated open-pollination grown in a controlled environment in Zuidwolde, The Netherlands in July, 2008.

Asexual reproduction of the new *Echinacea* plant by micropropagation a controlled environment in Heerhugowaard, The Netherlands since July, 2008, has shown that the unique features of this new *Echinacea* plant are stable and reproduced true to type in successive generations.

SUMMARY OF THE INVENTION

Plants of the new *Echinacea* have been observed under all possible environmental conditions and cultural practices. The phenotype may vary somewhat with variations in environment such as temperature and light intensity, without, however, any variance in genotype.

The following traits have been repeatedly observed and are determined to be the unique characteristics of 'Guava Ice'. These characteristics in combination distinguish 'Guava Ice' as a new and distinct *Echinacea* plant:

1. Upright plant habit.
2. Moderately vigorous growth habit.
3. Freely basal branching habit.

4. Strong flowering stems.
5. Early and freely flowering habit.
6. Large anemone-type inflorescences with greyed red to red-colored ray florets and orange red-colored disc florets.
7. Good garden performance.

Plants of the new *Echinacea* can be compared to plants of the female parent selection. Plants of the new *Echinacea* differ from plants of the female parent selection in the following characteristics:

1. Plants of the new *Echinacea* have shorter flowering stems than plants of the female parent selection.
2. Plants of the new *Echinacea* are more freely flowering than plants of the female parent selection.
3. Plants of the new *Echinacea* and the female parent selection differ in ray floret color as plants of the female parent selection have dark pink-colored ray florets.

Plants of the new *Echinacea* can be compared to plants of *Echinacea hybrida* 'Hot Papaya', disclosed in U.S. Plant Pat. No. 21,022. In side-by-side comparisons, plants of the new *Echinacea* differed from plants of 'Hot Papaya' primarily in ray floret coloration as plants of 'Hot Papaya' had orange red-colored ray florets.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet comprises a side perspective view of a typical flowering plant of 'Guava Ice' grown in a container.

The photograph on the second sheet is a close-up view of a typical inflorescence of 'Guava Ice'.

The photograph on the third sheet is a close-up view of the upper surface of a typical leaf of 'Guava Ice'.

DETAILED BOTANICAL DESCRIPTION

The aforementioned photographs and following observations and measurements describe plants grown during the late summer in an outdoor nursery in Zuidwolde, The Netherlands and under conditions and practices which approximate those generally used in commercial *Echinacea* production. During the production of the plants, day temperatures ranged from 12° C. to 26° C. and night temperatures ranged from 4° C. to 16° C. Measurements and numerical values represent averages for typical flowering plants. Plants were six months old when the photographs and description were taken. In the following description, color references are made to The Royal Horticultural Society Colour Chart, 2007 Edition, except where general terms of ordinary dictionary significance are used.

Botanical classification: *Echinacea hybrida* 'Guava Ice'.

Parentage:

*Female parent*.—Proprietary selection of *Echinacea hybrida* identified as code number Ec 512-004, not patented.

*Male parent*.—Unknown selection of *Echinacea hybrida*, not patented.

Propagation:

*Type*.—By micropropagation.

*Time to initiate roots, summer*.—About one week at 25° C.

*Time to produce a rooted young plant, summer*.—About five weeks at 21° C.

*Root description*.—Fine, fibrous; pale cream in color.

*Rooting habit*.—Freely branching; moderately dense.

Plant description:

*Plant form/growth habit*.—Herbaceous perennial; upright and columnar plant habit, narrow inverted triangle; freely basal branching habit; moderately vigorous growth habit.

*Plant height*.—About 70 cm.

*Plant diameter or spread*.—About 56.6 cm.

*Basal branches*.—Length: About 38.7 cm. Diameter: About 5 mm. Internode length: About 5.6 cm. Aspect: Erect to about 15° from vertical. Strength: Strong. Texture: Sparsely pubescent, strigose; rough. Color: Close to 144A to 144B.

Foliage description:

*Arrangement*.—Alternate, simple.

*Length*.—About 18.7 cm.

*Width*.—About 5 cm.

*Shape*.—Narrowly ovate to narrowly elliptic.

*Apex*.—Narrowly acute.

*Base*.—Long attenuate to narrowly cuneate.

*Margin*.—Mostly entire with occasional shallow serrations.

*Texture, upper and lower surfaces*.—Sparsely pubescent, strigose; rough.

*Venation pattern*.—Pinnate.

*Color*.—Developing leaves, upper surface: Between 141A and 137A. Developing leaves, lower surface: Close to 137B to 137C. Fully expanded leaves, upper surface: Close to N137B; venation, close to 147C to 147D. Fully expanded leaves, lower surface: Between 137C and 147B; venation, close to 147D.

*Petioles*.—Length: About 7.3 cm. Diameter: About 3 mm. Texture, upper and lower surfaces: Smooth, glabrous. Color, upper surface: Close to 144B. Color, lower surface: Close to 144A to 144B.

Inflorescence description:

*Appearance*.—Rotate anemone-type inflorescence form with ray and disc florets arranged acropetally on a capitulum; inflorescences positioned upright above the foliar plane on strong peduncles.

*Quantity of inflorescences per plant*.—About 30.

*Fragrance*.—None detected.

*Time to flower*.—Plants flower continuously from early July to late September in The Netherlands.

*Inflorescence longevity*.—Inflorescences maintain good substance for about three weeks on the plant; inflorescences persistent.

*Inflorescence bud*.—Height: About 2 cm. Diameter: About 2.4 cm. Shape: Flattened globular. Color: Close to 187A becoming closer to 143A with development.

*Inflorescence size*.—Diameter: About 7.4 cm. Depth (height): About 4.9 cm. Disc diameter: About 5.7 cm. Receptacle height: About 1 cm. Receptacle diameter: About 1.1 cm. Receptacle color: Close to 155A to 155B.

*Ray florets*.—Length: About 4.5 cm. Width: About 8 mm. Shape: Narrowly oblanceolate, falcate. Apex: Praemorse. Base: Cuneate. Margin: Entire. Texture, upper and lower surfaces: Smooth, glabrous; longitudinally ridged. Number, of ray florets per inflorescence: About 19 arranged in a single whorl. Aspect: Drooping, about 40° from horizontal. Color: When opening, upper surface: Close to 37C to 37D and 39B; towards the apex, between 22A to 22C and 23C. When opening, lower surface: Close to 35C to 35D; towards the apex, close to 20B to 20C. Fully opened, upper surface: Between 180D and 39B; towards the apex, close to 20A. Fully opened, lower surface: Between 179C to 179D and 34D; towards the apex, close to 20A.

*Disc florets*.—Length: About 2.3 cm. Diameter: About 6 mm. Shape: Tubular, enlarged; apices praemorse. Number of disc florets per inflorescence: About 250. Texture, upper and lower surfaces: Smooth, glabrous. Color: Immature, inner surface: Between 35B to 35C and 37A. Immature, outer surface: Close to N34C. Mature, inner surface: Close to 34B; mid-section, close to 31C; towards the base, close to 29B to 29C. Mature, outer surface: Close to 34C to 34D; mid-section, close to 22B; towards the base, close to 22C to 22D.

*Receptacle spines*.—Quantity: One per disc floret. Shape: Acicular. Apex: Acute. Base: Attenuate. Texture: Smooth, glabrous. Color: Apex: Close to 34A to 34B. Mid-section: Close to 145A. Base: Close to 145D.

*Involucral bracts*.—Quantity per inflorescence: About 45 arranged in about three whorls. Length: About 9 mm. Width: About 2 mm. Shape: Narrowly ovate. Apex: Acute. Base: Cuneate. Margin: Entire. Texture, upper surface: Smooth, glabrous. Texture, lower surface: Sparsely pubescent along the margins. Color, upper surface: Close to N137B. Color, lower surface: Close to 143A.

*Peduncles*.—Length, terminal peduncle: About 11.4 cm. Diameter: About 4 mm. Strength: Strong. Aspect: Upright to about 25° from vertical. Texture: Sparsely pubescent, strigose. Color: Close to 145B to 145C; blotches, close to 144B to 144C; towards the apex, close to 143B to 143C.

*Reproductive organs*.—Androecium (present on disc florets only): Quantity per floret: About four. Filament length: About 2 mm. Filament color: Close to 165D. Anther shape: Lanceolate. Anther length: About 2 mm. Anther color: Close to 165A. Pollen amount: None observed. Gynoecium (present on ray and disc florets): Quantity per floret: One. Pistil length: About 5 mm. Stigma shape: Decurrent. Stigma color: Close to 200A to 200B. Style length: About 3 mm. Style color: Close to 200C to 200D. Ovary color: Close to 145D. Fruits/seeds: Fruit and seed development have not been observed.

Disease/pest resistance: Plants of the new *Echinacea* have not been shown to be resistant to pathogens and pests common to *Echinacea*.

Garden performance: Plants of the new *Echinacea* have exhibited good garden performance and tolerate rain and wind. Plants of the new *Echinacea* have been observed to tolerate high temperatures of about 45° C. and hardy to USDA Hardiness Zone 4.

It is claimed:

1. A new and distinct *Echinacea* plant named 'Guava Ice' as illustrated and described.

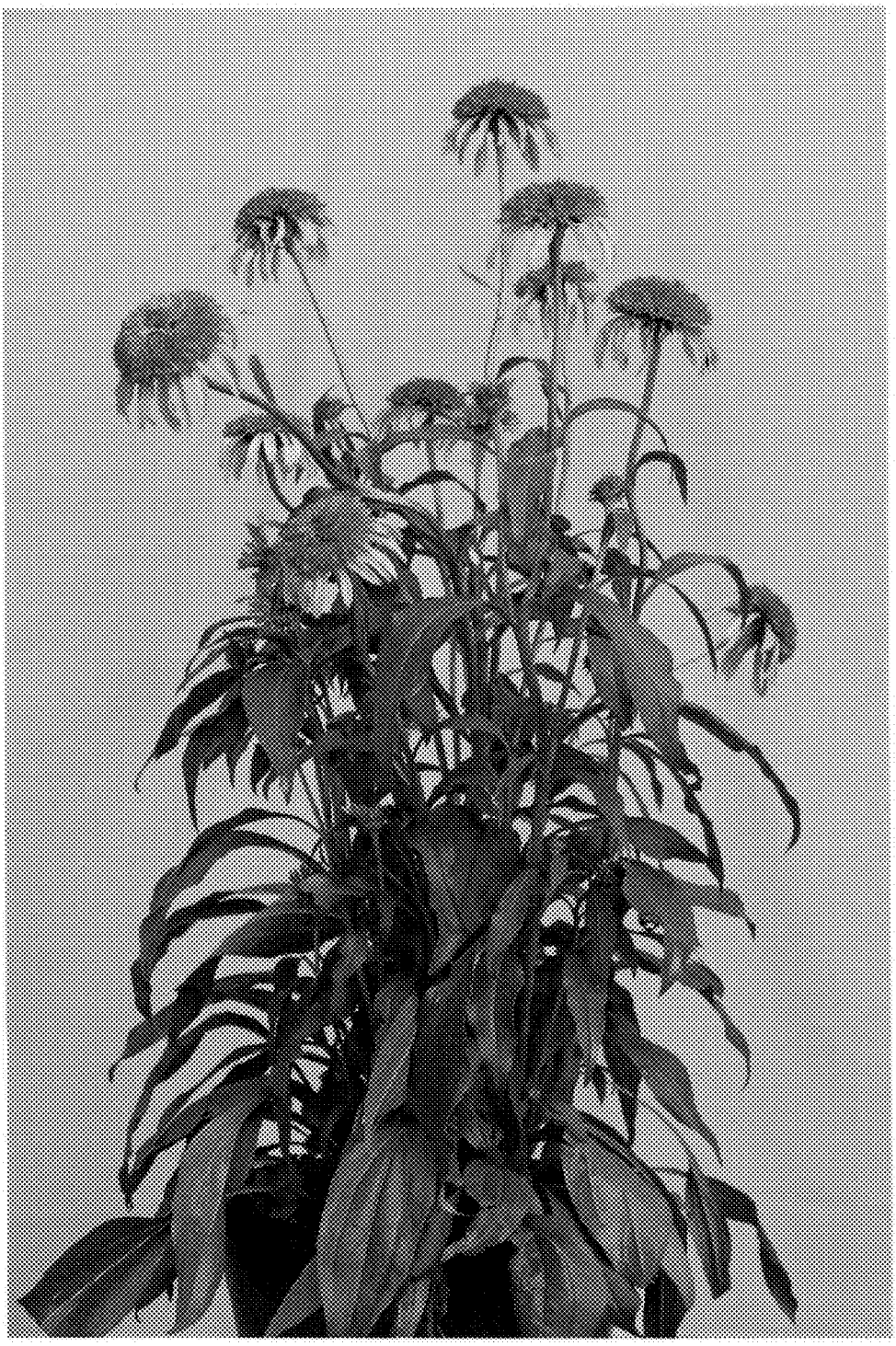

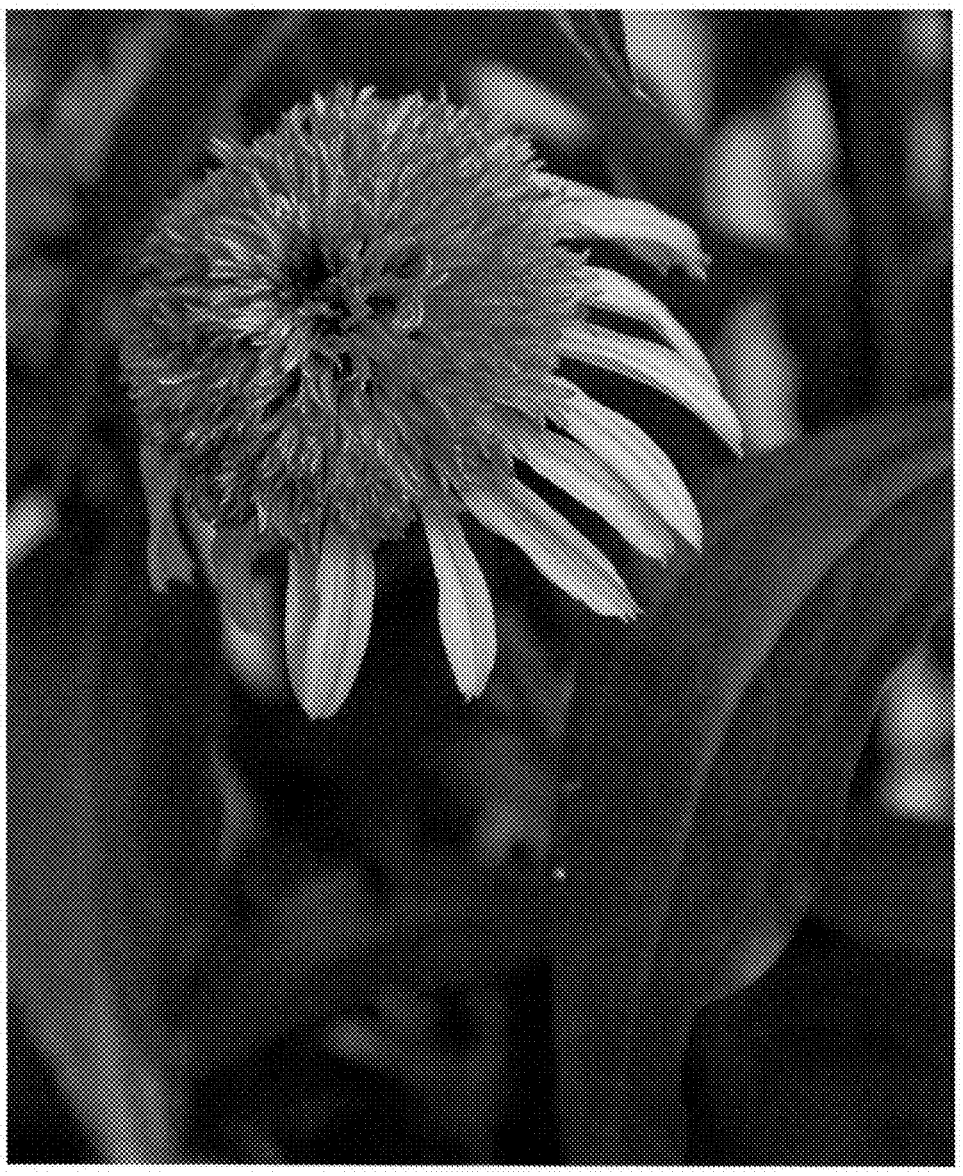

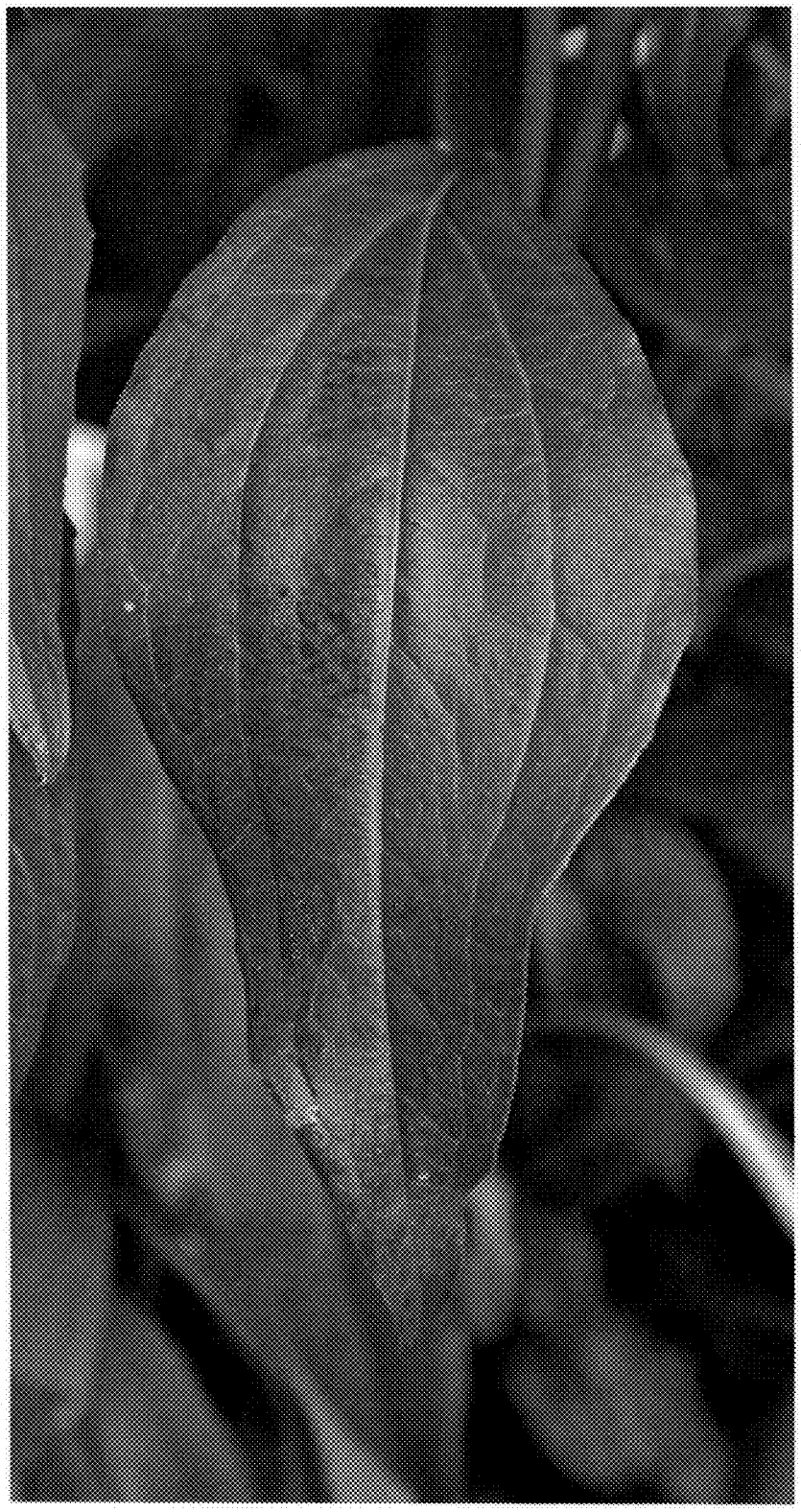

* * * * *